United States Patent [19]

Depel et al.

[11] Patent Number: 4,820,304
[45] Date of Patent: Apr. 11, 1989

[54] SPEECH PROSTHESIS DEVICE

[75] Inventors: William A. Depel, Lowell, Ind.; Bernd Weinberg, Tucson, Ariz.

[73] Assignees: Bivona, Inc., Gary; Purdue Research Foundation, West Lafayette, both of Ind.

[21] Appl. No.: 72,545
[22] Filed: Jul. 13, 1987
[51] Int. Cl.⁴ .............................................. A61F 2/20
[52] U.S. Cl. ....................................................... 623/9
[58] Field of Search ........................................... 623/9

[56] References Cited

U.S. PATENT DOCUMENTS 4,610,691  9/1986  Depel ..................................... 623/9
4,614,516  9/1986  Blom ...................................... 623/9

FOREIGN PATENT DOCUMENTS 0222509   5/1987  European Pat. Off. ............... 623/9
3211126  11/1982  Fed. Rep. of Germany ......... 623/9

Primary Examiner—Richard J. Apley
Assistant Examiner—James Prizant
Attorney, Agent, or Firm—Emrich & Dithmar

[57] ABSTRACT

A speech prosthesis device which is inserted into a surgically created opening communicating the trachea and esophagus of a laryngectomized patient includes a one-way valve assembly that permits air to be channeled air from the patient's trachea into the patient's esophagus while preventing flow of esophageal material into the trachea. The present invention provides an improvement in such prosthesis devices by providing that the membrane-like, tabbed flap or disc is seated at an angle which is oblique in reference to the longitudinal axis of the tubular housing of the device be, preferably, oval shaped, and that the tabbed flap or disk be superiorily hinged to the tubular housing. The predetermined and uniform resistance to airflow offered by the one-way valve assembly of the present invention is substantially less than the resistance offered by a normal human larynx.

23 Claims, 2 Drawing Sheets

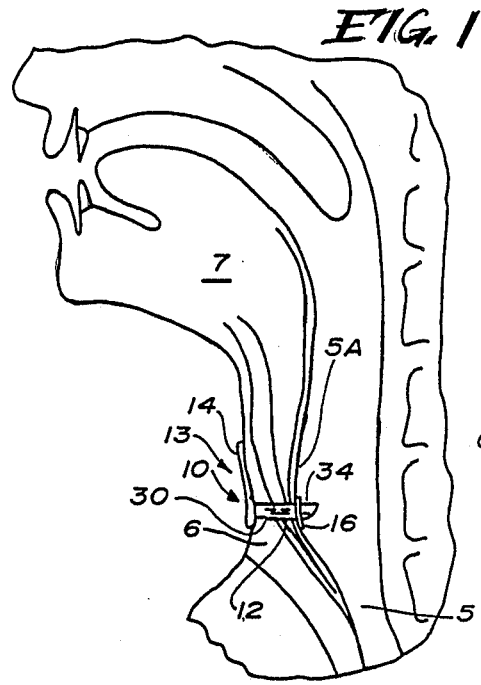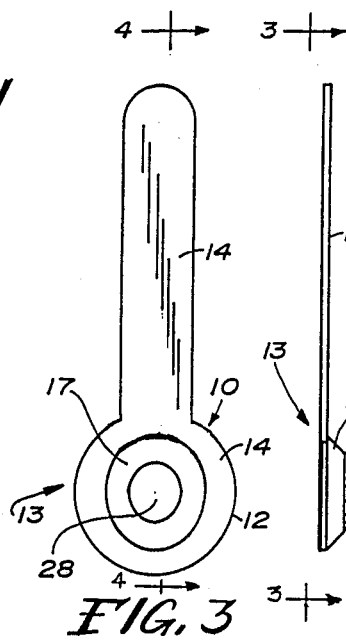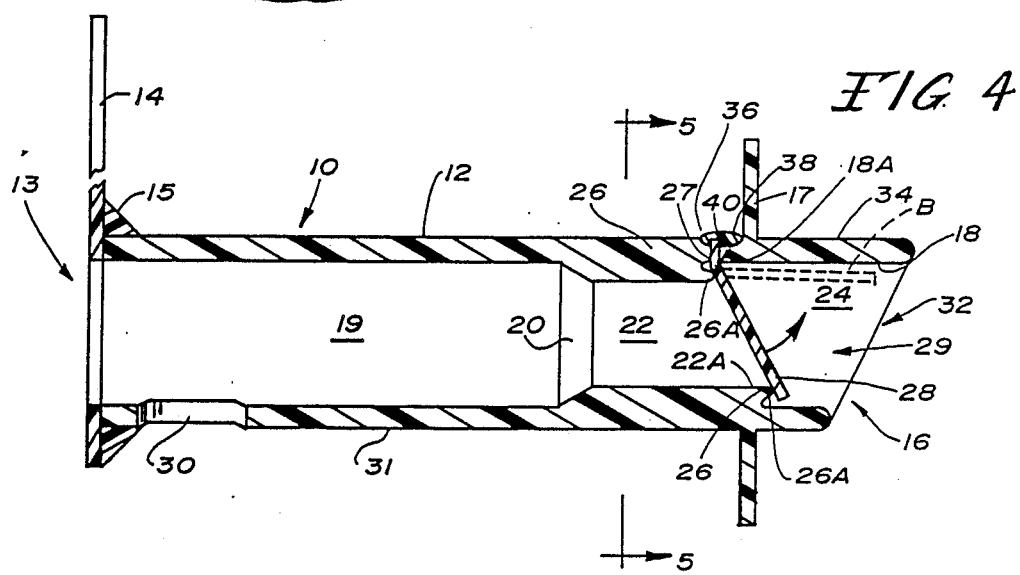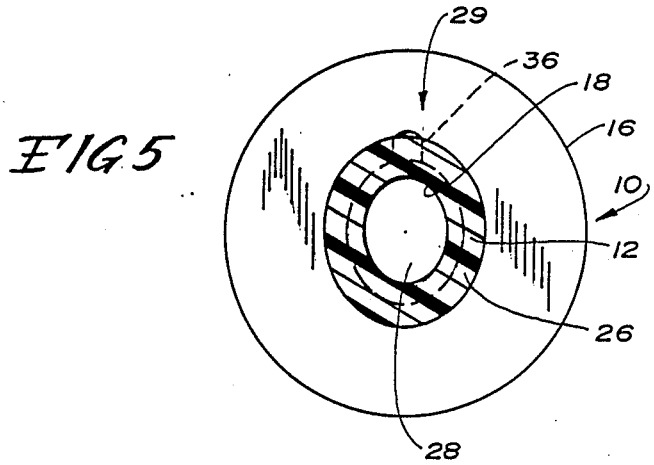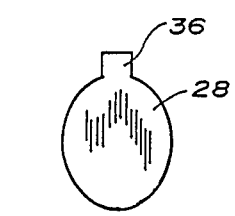

4,820,304
SPEECH PROSTHESIS DEVICE

BACKGROUND OF THE INVENTION

The present invention relates to a novel voice or speech prothesis device of the type which is inserted into a surgically created opening communicating the trachea and esophagus of a laryngectomized patient. Specifically, the invention relates particularly to the manner in which the membrane-like, tabbed flap or disc of a one-way flap-type valve is positioned within the tubular housing of the prosthetic device. The seating and superiorly hinged positioning of the flap of the check-valve provides that a significant degree of decreased resistance to airflow is obtained when the voice prosthesis device is constructed and formed in accordance with the teachings of the present invention.

Voice prostheses devices are known which may be inserted into a surgically created fistula between the trachea and esophagus of a laryngectomized patient and it is known that it is desirable for such devices to offer low resistance to air flow. Examples of voice prothesis devices embodying a flap-type check-valve are described in U.S. Pat. Nos. 4,435,853 and 4,610,691.

In particular, the U.S. Pat. No. 4,610,691 discloses that by selecting a particular modulus and hardness for the membrane-like flap or disc of the one-way check valves used in a voice prosthesis device, and by attaching or anchoring the periphery of each flap or disc adjacent to the prosthesis housing, voice prosthesis devices may be produced in commercial quantities, with a pre-determined uniform resistance to airflow which may be equal to, less than or greater than the resistance offered by the normal human larynx. However, when the modulus and hardness of the membrane-like flap or disc of the one way check-valve is selected to accomplish a resistance to air flow that is substantially less than that offered by the normal human larynx, the flap or disc may, on occasion, herniate through the seat valve. When the flap or disc does herniate beyond the valve seat, esophageal contents may enter the trachea and speech is impaired until or unless the herniated flap is returned to its correct position by air flow from the trachea through the device.

One object of the present invention is to provide a novel voice or speech prosthesis device having a one-way check-valve whose membrane-like, tabbed flap or disc is of sufficient modulus and hardness to prevent and substantially eliminate the occurrence of flap herniation beyond the valve seat while at the same time offering a resistance to airflow which is substantially below that offered by the normal human larynx.

Another object of the present invention is a novel prosthesis device having a one-way check-valve wherein its membrane-like, tabbed flap or disc is seated at an angle which is oblique in reference to the longitudinal axis of the tubular housing and which is superiorly hinged thereto to provide a speech prosthesis device possessing substantially less resistance to airflow than the resistance to airflow offered by the normal human larynx.

Still another object of the present invention is a novel voice or speech prosthesis device having a membrane-like, tabbed flap or disc seated within the tubular housing at an angle which is oblique in reference to the longitudinal axis of the tubular housing to provide a prosthesis device having a substantially decreased resistance to airflow as compared to that of a normal human larynx without resorting to altering the modulus and hardness of the material of the tabbed flap or disc to a point which invites herniation of the flap through its valve seat.

Still a further object of the present invention is a novel voice or speech prothesis device wherein the tubular housing may include a bullet or dome-shaped distal end which does not compromise the devices resistance to airflow through and which facilitates insertion of the speech prothesis device through the surgically created fistula.

For a more complete understanding of the scope and nature of the present invention, reference may now be had to the accompanying drawings and the following detailed description of the presently preferred embodiments of the present invention.

BRIEF DESCRIPTION OF THE DRAWINGS

FIG. 1 is a diagrammatic view showing a speech prosthesis device in accordance with the present invention inserted into a surgically created opening communicating the trachea and esophagus of a laryngectomized patient;

FIG. 2 is an enlarged side elevational view of the speech prosthesis device shown in FIG. 1;

FIG. 3 is an end elevational view taken along line 3—3 of FIG. 2;

FIG. 4 is a fragmentary longitudinal sectional view taken on line 4—4 of FIG. 3;

FIG. 5 is a sectional view taken along line 5—5 of FIG. 4;

FIG. 6 is an elevational view of a membrane-like, tabbed flap or disc valve member forming a component of the speech prosthesis device in accordance with the present invention;

DESCRIPTION OF THE PREFERRED EMBODIMENTS

Figure 7:
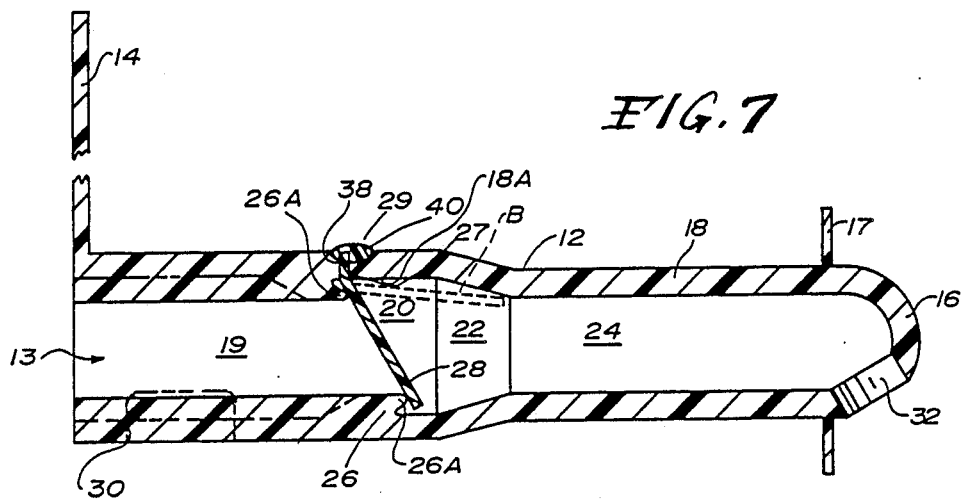
FIG. 7 is a fragmentary longitudinal sectional view of a speech prosthesis device in accordance with another embodiment of the present invention.

Referring now to the drawings in greater detail, wherein like numerals have been used to designate the same or similar parts, there is illustrated in FIG. 1 an esophagus 5 and trachea 6 of a laryngectomized patient 7. The patient 7 is provided with a surgically created opening (not shown) between the treachea 6 and the esophagus 5 for receiving the voice or speech prosthesis device 10 therein, in accordance with the present invention.

The voice or speech prosthesis device 10 includes a tubular body or housing 12 which may be injection molded in a known manner from a medical grade silicone material or other similar type material. An outer or proximal end 13 of the device 10 is exposed after placement and retained in position by a single, vertically upwardly extending skin-adherent positioning tab 14. However, the device may include more than on positioning tab 14 on the proximal end 13. The proximal end 13 of the housing 12 is open to facilitate speech when the device is used in conjunction with a tracheostoma valve to facilitate speech as is known in the art. A flange 15 may be located along the outer end 13 of the housing 12 and forms a base of increased area for the positioning tab 14 thereon. Adjacent an inner or distal end 16 of the tubular body or housing 12 is an integral annular retaining flange 17 which engages the front wall 5A of the esophagus 5, as shown in FIG. 1, to retain the speech prosthesis device in position.

As illustrated in FIGS. 2-5, a bore 18 extends through the tubular housing 12 and is comprised of four sections 19, 20, 22 and 24. The bore section 19 extends from the outer or proximal end 13 of the housing 12 inwardly to a frusto-conical shaped transition section 20, which joins the section 19 to a shorter and smaller-in-diameter section 22. An inner end 22A of the section 22 joins a larger-in-diameter bore section 24 adjacent the inner or distal end 16 of the housing 12 at a circumferentially extending shoulder 26. The bore 18 is provided with a small opening 27 through the upper surface 18A.

The circumferentially extending shoulder 26, as illustrated in FIGS. 4, 7, 8 and 9 is pitched approximately 120° from the longitudinal axis of the bore 18, with the plane of the seating shoulder 26A forming a valve seat 26 for a membrane-like, tabbed flap or valve disc 28 which forms the moving part of a one-way check valve 29 of the voice prosthesis device 10. The plane of the valve seat 26 is inclined relative to the longitudinal axis of the tubular housing 12 by an amount sufficient to substantially reduce the resistance of the check valve to the flow of air therethrough without substantial flexing of the valve disc 28 as the valve opens. The flap or valve disc 28 is flexible and may be formed of a water-resistant material such as silicon rubber or other similar material. The tubular body or housing 12 and the tabbed flap or valve disc 28 are, preferably, shown in the illustrated embodiment as being oval in cross-section, but this is not considered limiting to the scope of the present invention.

The oval-shaped tubular body 12 may have an elongated air inlet port 30 in an underside 31 thereof (the side opposite that from which the positioning tab 14 extends) which provides air passage means between the trachea 6 through the check valve assembly 29, the bore 18 and into the esophagus 5. However, if the device 10 is used with a tracheostoma valve attached to the proximal end 13, then the device 10 would not include an air inlet port 30. It will be seen that the inner or distal end 16 of the bore section 24 is open to provide an air outlet port 32 which opens into the esophagus 5. The one way-check valve assembly 29 comprising the tabbed flap or disc 28 and its cooperation with the valve seating shoulder 26A serves to allow air to be channeled from the trachea 6 into the esophagus 5 during the speech process and at other times, closes off communication between the esophagus 5 and trachea 6 to prevent flow of esophageal content (gaseous, liquid and/or solid) from the esophagus 5 into the trachea 6. The inner or distal end 16 of the housing 12 is slanted, preferably at an angle of approximately 45 degrees, to facilitate insertion of the device 10 through the surgically created opening provided therefor and further to provide an overhang or hood portion 34 along the top surface of the inner or distal end 16 which serves as a shield for the bore section 24 to prevent materials passing downwardly through the esophagus 5 from entering bore section 24 and The present invention is particularly concerned with the manner in which the membrane-like, tabbed valve flap or disc 28 is positioned and mounted within the housing 12. In FIGS. 4-6 and 7-8 it will be noted that the oval shaped valve flap or disc 28 has a tab-like extension or projection portion 36 extending integrally therefrom. The housing or body 12 is provided with an outwardly diverging aperture 38 on its upper surface, positioned slightly outwardly of the retaining flange 17, and approximately above the valve seating shoulder 26A for receiving the tab or projection portion 36 of the valve disc 28. The aperture 38 is most restricted at its inner or lower end where it engages the upper surface 18A of the bore 18 and it has approximately the same dimension as the cross-section of the tab 36, while allowing the projection 36 to be readily inserted upwardly therethrough.

After the projection portion 36 of the valve flap of disc 28 has been fully inserted into aperture 38 in the body 12, a drop of moisture-resistant cement 40 is deposited into the recess formed by the aperture 38, thereby securing the projection 36 firmly in place and sealing off the aperture 38.

Figure 8:
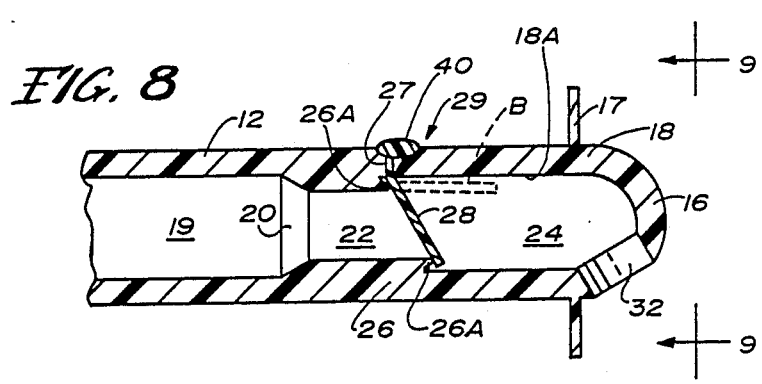
FIG. 8 is a fragmentary longitudinal sectional view of a speech prosthesis device in accordance with another embodiment of the present invention.
Figure 9:
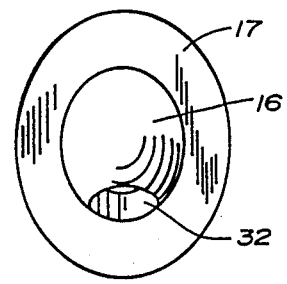
FIG. 9 is an end elevational view taken along lines 9—9 of FIG. 8.

As shown in FIGS. 4, 7 and 8, the valve flap or disc 28 is normally seated against the valve seating shoulder 26A in the closed portion. In this respect, the seating shoulder 26A, along its uppermost extent, forms an abutment 26 against which the upper periphery, at its juncture with the projection 36, of the disc 28, presses. This pressure, as illustrated, causes the disc 28 to bend slightly inwardly toward the inner end 16 of the device 10 and produces a hinge formation between the projection 36 and the disc 28 and causes the disc 28 to seat itself against the annular seating shoulder 26A around the circumference of the tubular housing 12. When the pressure on both sides of disc 28 is equal, the disc 28 seals against the annular seating shoulder 26A and the check valve assembly 29 is closed. When the valve assembly 29 is closed, the plane of valve seat is inclined relative to the axis of the tubular housing by an amount sufficient to substantially reduce the resistance of the valve assembly to the flow of air therethrough without substantial flexing of the valve disc 28 as the valve opens. Such bending of the disc 28 further prevents the disc 28 from bending or herniating backwards, past the annular seating shoulder 26A, into the bore section 22 upon severe pressure differential being created on both sides of the disc 28, such as during the production of a hiccup, to prevent the disc 28 from herniating beyond the annular seating shoulder 26A.

However, when there is a sufficient differential in pressure on opposite sides of the disc 28, as creating during the speech process, producing a flow of air from the trachea 6 toward the esophagus 5, the flap or disc 28 will pivot or hinge upwardly at the juncture between the projection 36 and the periphery of the flap or disc 28, thereby coming unseated from the valve seating shoulder 26 and allowing air to flow through the bore 18 of the device 10 and enter the esophagus 5 for the production of speech. In FIGS. 4, 7 and 8, the open position wherein the disc 28 is moved away from the annular seating shoulder 26A is shown in dotted lines, as position B, during the speech process.

The oval shaped structure of the annular seating shoulder, disc and tubular housing permits the movement of the disc 28 from the closed to the open position, a position wherein the disc is positioned substantially parallel to the axis of the tubular housing, as shown as position B in FIGS. 4, 7 and 8. This provides a more sensitive voice or speech prosthesis device than has been heretofore obtainable.

The tubular housing or body 12 and the valve flap or disc 28 is produced on a production basis so as to meet appropriate specifications and tolerances. Thus, the housing 12 and valve member 28 is produced on a quantity production basis to permit duplicity for all practical purposes.

It will be appreciated that the assembly of the membrane-like flaps or discs 28 into the valve housings or bodies 12 is such that the resulting assemblies will be substantially identical. Furthermore, because the hinging or pivoting action of the oval flap or disc 28 occurs at an identical position from assembly to assembly, the resistance to airflow from the one-way check valve or assembly 29, and in turn the prosthesis device 10, is uniform and duplicatable.

FIGS. 7 and 8 illustrate additional embodiments of the voice or speech prosthesis device 10 which incorporate the novel one-way check valve assembly 29 in accordance with the present invention. Basically, FIGS. 7 and 8 illustrate voice or speech prosthesis devices having various inside and outside diameter French sizes. Each device includes a tubular housing 12 which is comprised of sections 19, 20, 22 and 24. In FIG. 7, section 19 extends to the annular pitched seating shoulder 26A which provides a valve seat 26 for tabbed flap or disc 28 which provides the one-way check valve assembly 29, in accordance with the present invention. In FIG. 8, section 22 extends to the annular seating shoulder 26A. Each of the voice or voice prosthesis devices 10 of FIGS. 7 and 8 include a bullet or dome-shaped inner or distal end 16, having an opening 32 therein which cooperates with the sections 19, 20, 22 and 24, to permit airflow into the esophagus 5. The bullet or dome-shaped inner or distal end 16 prevents materials in the esophagus 5 from entering bore section 24 and facilitates insertion of the prosthesis device 10 into the surgical fistula between the trachea and esophagus.

The actual resistance to airflow offered by the check valve 29 of the present invention is dependent upon several factors. One factor is the area and shape of the integral connection between the oval-shaped valve flap or disc 28 and its projection 36. Another factor is the nature of the particular material utilized in the formation of the disc 28. Another factor is the positioning of the annular seating valve within the tubular housing which is inclined approximately 120° from the axis of the tubular housing which engages the tabbed flap or disc 28 to position the disc at an angle approximately 30° from the vertical. Thus, although approximately 120° is a preferred angle, it is within the scope of the present invention that the angle be oblique with respect to the axis of the tubular housing. However, it is merely sufficient that the plane of the annular valve seat be inclined relative to the axis of the tubular housing by an amount sufficient to substantially reduce the resistance of the valve assembly to the flow of air therethrough without substantial flexing of the valve disc as the valve opens. Upon optimizing these variables, it has been empirically found that a voice or speech prosthesis device 10 made in accordance with the teachings of the present invention will provide a decreased resistance to airflow, of at least 30 percent below that resistance found in prior art low resistance prior art devices. Such a decreased resistance to airflow is necessary for some laryngectomy patients, such as those, for example, with respiratory difficulties.

The ultra-low resistance provided by the voice or speech prosthesis device 10 in accordance with the present invention is best illustrated by comparing the resistance of the present disclosed invention to the resistance of a known prosthesis device, as manufactured in accordance with the disclosure in U.S. Pat. No. 4,610,691.

Set forth in Table I are the measured resistances at various flow rates for both the voice or speech prosthesis device of the present invention (Ultra Low) and the voice prosthesis device disclosed in U.S. Pat. No. 4,610,691 (Low).

TABLE I

ULTRA LOW RESISTANCE
TRACHEOESOPHAGEAL PUNCTURE PROSTHESIS

| Flow Rate (LPS) | Valve Resistance (cm H2O/LPS) | |
|---|---|---|
| Mean Resistance (10 Devices) | | |
| 0.10 | 25.3 | |
| 0.15 | 22.7 | |
| 0.21 | 21.0 | |
| 0.26 | 20.0 | |
| 0.31 | 19.6 | |
| U.S. PAT. NO. 4,610,691 (LOW) | | |
| Flow Rate (LPS) | Valve Resistance (cm H2)/LPS) | % Change Ultra Low v. Low |
| Mean Resistance (20 Devices) | | |
| 0.10 | 37.1 | 32 |
| 0.16 | 35.1 | 35 |
| 0.21 | 33.9 | 38 |
| 0.26 | 33.9 | 39 |

As shown, a marked decrease (of at least 30%) to airflow resistance is obtained over the prior art low resistance device.

It will be understood that certain changes and modifications can be made to the voice or speech prosthesis device of the present invention without departing from the teachings of the present invention. Accordingly, the scope of the invention is only to be limited as necessitated by the accompanying claims.

We claim:

1. A speech prosthesis device which may be used with a treacheostoma valve and adapted to be placed in a surgically created opening between the trachea and esophagus and including a tubular housing having a proximal end and a distal end, an air inlet opening on the proximal end adapted to cooperate with the tracheostoma valve, an air outlet at the distal end opening into the esophagus, and a one-way check valve assembly positioned between said inlet port and said outlet, said one-way check valve assembly comprised of an annular valve seat positioned within said housing and a membrane-like oval-shaped tabbed valve disc anchored adjacent its periphery to said housing so as to close against said annular valve seat when necessary to prevent entry of esophageal content into the trachea through said housing, the improvement comprising:

wherein the plane of said annular valve seat is inclined relative to the longitudinal axis of the tubular housing by an amount sufficient to substantially reduce the resistance of the valve assembly to the flow of air therethrough without substantial flexing of said valve disc as the valve disc is opened, and wherein said valve disc includes at least one tab portion which is anchored superiorly to said tubular housing to permit pivotal movement of said valve disc between an open position and a closed position with respect to said annular valve seat.

2. The device of claim 1 wherein said tubular housing and said annular seat are oval-shaped in cross-section.

3. The device of claim 2 wherein said tubular housing is a unitary structure which is injection molded.

4. The device of claim 3 wherein said tubular housing is made of silicon material.

5. The device of claim 1 wherein said distal end of said tubular housing is dome-shaped to faciitate insertion of the prosthesis device through the surgically created opening and said opening therein is sized to be substantially equal to the interior diameter of said tubular housing and said opening is inferiorly located on said distal end.

6. The device of claim 1 wherein said check valve assembly is provided with an airflow resistance which is less that the resistance of about 35 centimeters of water pressure.

7. The device of claim 1 wherein said valve disc is positioned substantially parallel to the plane of the longitudinal axis of the tubular housing when said valve assembly is in the open position.

8. The device of claim 1 wherein said tubular housing includes an annular positioning flange located adjacent said distal end for retaining the device within the surgical fistula.

9. The device of claim 1 wherein said valve assembly is closed during periods of equal pressure on either side of said valve assembly.

10. The device of claim 1 wherein said valve assembly is open whenever the patient is speaking.

11. The device of claim 1 wherein said annular valve seat comprises a shoulder which is circumferentially disposed within the tubular housing at an angle which is oblique with respect to the longitudinal axis of said tubular housing.

12. The device of claim 11 wherein said shoulder includes an upper portion which abuts against said membrane-like tabbed valve disc to position said valve disc at an angle which is oblique with respect to the longitudinal axis of said tubular housing when said valve disc is in the closed position.

13. The device of claim 12 wherein said angle is approximately 120° with respect to the longitudinal axis of said tubular housing.

14. A speech prosthesis device to be placed in a surgically created opening between the trachea and esophagus and including a tubular housing having a proximal end and a distal end, an air inlet into the trachea and an air outlet at the distal end opening into the esophagus, and a one-way check valve assembly positioned between said inlet port and said outlet, said one-way check valve assembly comprised of an annular valve seat positioned within said housing and a membrane-like oval-shaped tabbed valve disc anchored adjacent its periphery to said housing so as to close against said annular valve seat when necessary to prevent entry of esophageal content into the trachea through said housing, the improvement comprising:

wherein the plane of said annular valve seat is inclined relative to the longitudinal axis of the tubular housing by an amount sufficient to substantially reduce the resistance of the valve assembly to the flow of air therethrough without substantial flexing of said valve disc as the valve disc is opened, and wherein said valve disc includes a tab portion which is anchored to the top of said tubular housing to permit pivotal movement of said valve disc between an open position and a closed position with respect to said annular valve seat.

15. The device of claim 14 wherein said tubular housing and said annular valve seat are oval-shaped in cross-section.

16. The device of claim 14 wherein said distal end of said tubular housing is dome-shaped to facilitate insertion of the prosthesis device through the surgically created opening and said opening therein is inferiorly located in said distal end.

17. The device of claim 14 wherein said valve disc is positioned substantially parallel to the plane of the longitudinal axis of the tubular housing when said valve assembly is in the open position.

18. The device of claim 14 wherein said check valve assembly is provided with an airflow resistance which is less than the resistance of about 35 centimeters of water pressure.

19. The device of claim 14 wherein said tubular housing includes at least one positioning tab on an externally extending end thereof for external attachment of the device to the patient.

20. The device of claim 14 wherein said tubular housing includes an annular positioning flange located adjacent said distal end for retaining the device within the surgically created opening.

21. The device of claim 14 wherein said annular valve seat comprises a shoulder which is circumferentially disposed within the tubular housing at an angle which is oblique with respect to the longitudinal axis of said tubular housing.

22. The device of claim 21 wherein said shoulder includes an upper portion which abuts against said membrane-like tabbed valve disc to position said valve disc at an angle which is oblique with respect to the longitudinal axis of said tubular housing when said valve disc is in the closed position.

23. The device of claim 22 wherein said angle is approximately 120° with respect to the longitudinal axis of said tubular housing.

* * * * *